United States Patent [19]

Ahmed

[11] Patent Number: 4,894,201
[45] Date of Patent: Jan. 16, 1990

[54] NUCLEAR FUEL PELLET SURFACE DEFECT INSPECTION APPARATUS

[75] Inventor: Hassan J. Ahmed, Columbia, S.C.

[73] Assignee: Westinghouse Electric Corp., Pittsburgh, Pa.

[21] Appl. No.: 199,735

[22] Filed: May 27, 1988

[51] Int. Cl.$^4$ ............................................. G21C 19/00
[52] U.S. Cl. ..................................... 376/261; 376/245; 73/622; 209/590; 53/504
[58] Field of Search ............... 376/261, 260, 248, 252, 376/258, 245, 159, 257; 73/622, 618; 209/590, 576; 53/504, 500; 29/723, 906; 193/2 R, 38, 41

[56] References Cited

U.S. PATENT DOCUMENTS

| | | | |
|---|---|---|---|
| 2,635,746 | 4/1953 | Gordon | 209/72 |
| 2,859,610 | 11/1958 | Dickey | 209/590 |
| 3,029,943 | 4/1962 | Diamond et al. | 209/590 |
| 3,183,709 | 5/1965 | Rankin et al. | 73/622 |
| 3,272,332 | 9/1966 | Jones | 209/75 |
| 3,712,469 | 1/1973 | Dwyer et al. | 209/111.7 |
| 3,907,123 | 9/1975 | Howell | 53/531 |
| 3,969,228 | 7/1976 | Browning | 209/73 |
| 3,975,261 | 8/1976 | Beck | 209/74 M |
| 4,037,103 | 7/1977 | Ryden, Jr. | 250/341 |
| 4,193,502 | 3/1980 | Marmo | 209/555 |
| 4,208,915 | 6/1980 | Edwards | 73/620 |
| 4,212,398 | 7/1980 | Parker et al. | 209/590 |
| 4,243,078 | 1/1981 | Sahlin | 53/473 |
| 4,268,808 | 5/1981 | Melngailis | 333/195 |
| 4,349,112 | 9/1982 | Wilks et al. | 209/538 |
| 4,468,163 | 8/1984 | King et al. | 414/21 |
| 4,557,386 | 12/1985 | Buckley et al. | 209/556 |
| 4,576,286 | 3/1986 | Buckley et al. | 209/558 |
| 4,628,736 | 12/1986 | Kirby et al. | 73/590 |
| 4,677,852 | 7/1987 | Pinyan et al. | 73/628 |
| 4,690,284 | 9/1987 | Buckley et al. | 209/590 |
| 4,819,783 | 4/1989 | Pinyan et al. | 209/590 |

OTHER PUBLICATIONS

Publication "Inspector General User's Guide" Dated Aug. 1987; Cochlea Corporation.

Primary Examiner—Daniel Wasil
Attorney, Agent, or Firm—L. A. DePaul

[57] ABSTRACT

A modified inspection apparatus for inspecting nuclear fuel pellets for surface defects includes a pellet guide chute assembly extending through an ultrasonic inspection chamber. The guide chute assembly has a support substrate and a pair of elongated plates attached on respective upper adjacent sides of the substrate. The substrate is composed of a pair of elongated wall sections rigidly attached together to have a V-shaped configuration in cross section. The plates are adjustably attached on the substrate wall sections for supporting a nuclear fuel pellet between and on adjacent longitudinal portions of the plates located in the inspection chamber. The plates have respective slots and cutout regions underlying the pellet at the adjacent longitudinal portions of the plates so as to expose portions of the support substrate wall sections also underlying the pellet such that acoustical energy can be propagated to and from bottom and side portions of the pellet via reflection of the acoustical energy from the exposed wall section portion. Also, an acoustical energy reflecting cover is disposed over the guide chute assembly at the inspection chamber. Further, a pellet position sensing arrangement and a transducer array for transmitting and receiving acoustical energy are included in the modified inspection apparatus.

13 Claims, 8 Drawing Sheets

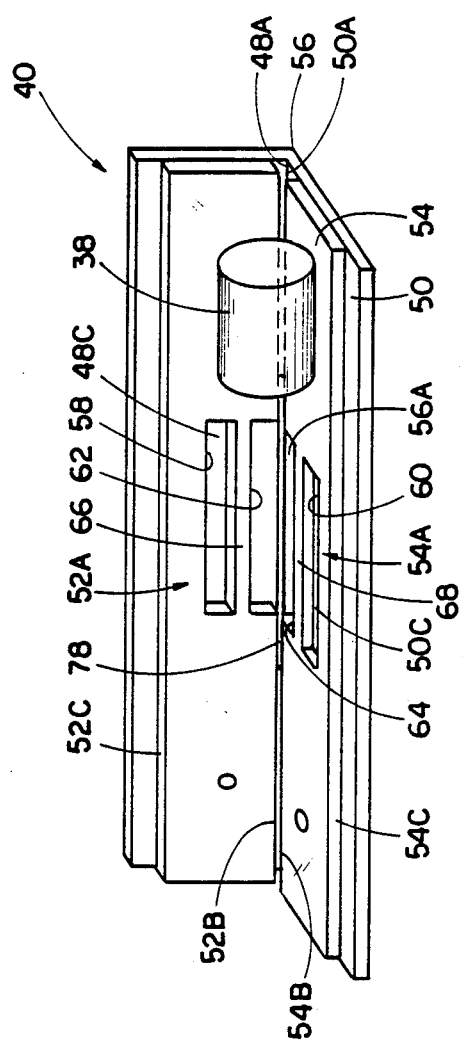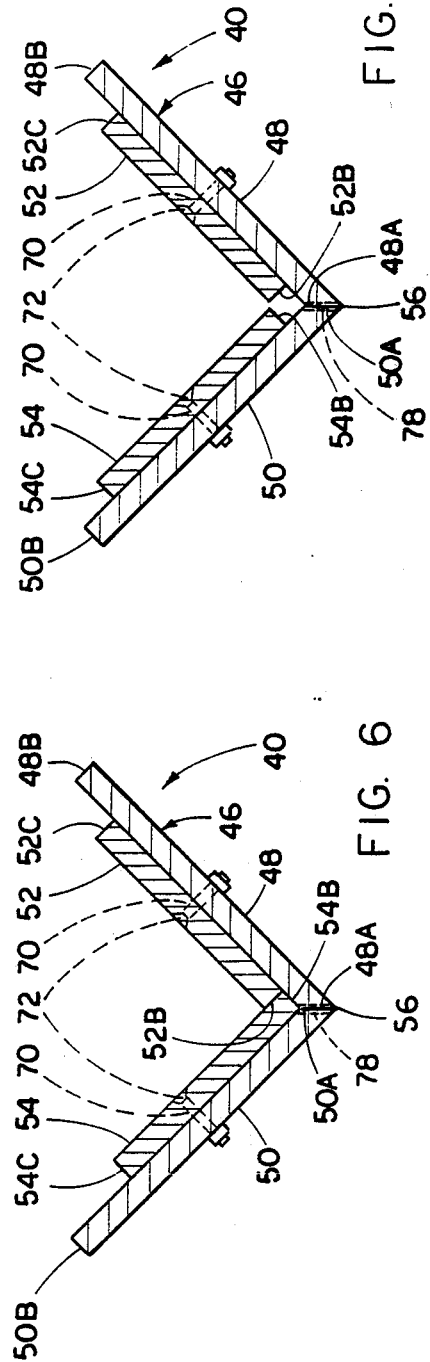

NUCLEAR FUEL PELLET SURFACE DEFECT INSPECTION APPARATUS

CROSS REFERENCE TO RELATED APPLICATION

Reference is hereby made to the following copending U.S. patent application dealing with related subject matter and assigned to the assignee of the present invention: "Improved Nuclear Fuel Pellet Diameter Measurement Apparatus" by Hassan J. Ahmed et al, assigned U.S. Pat. Ser. No. 942,013 and filed Dec. 12, 1986, a continuation of U.S. Pat. Ser. No. 642,609, filed Aug. 20, 1984 and now abandoned.

BACKGROUND OF THE INVENTION

1. Field of the Invention

The present invention relates generally to nuclear fuel pellet inspection and, more particularly, is concerned with an improved apparatus for inspecting fuel pellets for surface defects.

2. Description of the Prior Art

Nuclear reactors include fuel assemblies which contain pellets of fissionable material as their basic fuel element. In one exemplary embodiment, a pellet ideally takes the form of a right cylinder with slightly concave or dished opposite ends. For incorporation into fuel assemblies, a number of pellets are stacked end to end in a fuel rod cladding tube which, like the pellets, is usually of circular cross-section. Then, a given number of fuel rods are grouped together in a fuel assembly.

It is essential that all pellets used in the fuel assembly be free of circumferential defects, such as cracks and chips, in order to achieve desired stacking of the pellets within the fuel rod tube as well as uniform heat transfer between the stacked pellets and cladding tube and uniform consumption of the pellets during operation of the reactor core. Consequently, an important step in the manufacture of the nuclear fuel pellet is the inspection of its surface to ascertain whether there are any defects present.

Exemplary prior art systems for inspecting and classifying nuclear fuel pellets are disclosed in U.S. Pat. Nos. to Jones (3,221,152; 3,272,332; and 3,282,116), Ryden, Jr. (4,037,103), Marmo (4,193,502), and Wilks et al (4,349,112). While the inspection systems of these prior art patents appear to achieve their objectives under the range of operating conditions for which they were designed, none of these systems appear to be adapted to perform inspection of a pellet for circumferential or surface defects.

One commercial inspection apparatus, sold under the registered trademark, Inspector General, by Cochlea Corporation of San Jose, Calif., for inspecting and sorting small parts uses non-contact, three-dimensional ultrasonic vision to verify the identity, shape, defects, orientation, and sequence of parts. Its overall objective is to acoustically detect and cull out parts with shape defects. For a detailed understanding of this Cochlea Corporation inspection apparatus, attention is directed to a publication entitled "Inspector General User's Guide" dated Aug. 1987 and to U.S. Pat. Nos. to Buckley et al (4,557,386; 4,576,286; and 4,690,284) and Pinyan et al (4,677,852) assigned to Cochlea Corporation.

Basically, inspection by this apparatus is accomplished while the parts are in transit. The parts to be inspected are fed down a chute from a vibratory bowl feeder by a singulation device. As each part is in transit, it is exposed to 40 kHz sound waves emanating from suitably positioned emitters. The waves bounce off the part, and the reflections are then picked up by an array of transducers or sensors. Analysis of reflected sound waves gives each part an unique "acoustic signature", which is compared to a previously "learned" good part signature. Acceptance or rejection is based on that comparison. This acoustically-based system is said to outperform and be more versatile than more traditional vision, laser, tactile and proximity-sensing techniques.

However, in its approach to parts handling and positioning, this "off-the-shelf" inspection apparatus is designed for general purpose parts inspection and sorting and thus cannot be used directly without modification, to inspect nuclear fuel pellets. Consequently, a need exists for modifications to this inspection apparatus which will dedicate it to nuclear fuel pellet inspection.

SUMMARY OF THE INVENTION

The present invention provides a fuel pellet surface defect inspection apparatus designed to satisfy the aforementioned needs. In the inspection apparatus of the present invention, certain improvements are incorporated therein relating to the positioning of pellets in an ultrasonic inspection chamber of the apparatus. These improvements adapt or dedicate the apparatus for inspection of fuel pellets for surface defects such as chips and cracks.

Accordingly, the present invention is set forth in an apparatus for inspecting nuclear fuel pellets for surface defects and having an inspection chamber. The present invention relates to a pellet guiding chute which comprises: (a) a support substrate composed of a pair of elongated wall sections each having a pair of opposite spaced longitudinal edges, the wall sections being rigidly attached together along adjacent ones of the longitudinal edges to form a corner and being angularly displaced from one another at remote ones of the longitudinal edges to have a generally V-shaped configuration in cross section; (b) a pair of elongated plates respectively disposed on upper adjacent sides of the support substrate wall sections; and (c) means for adjustably attaching the plates to the wall sections for sliding movement thereon toward and away from the adjacent longitudinal edges thereof to locate the plates at desired stationary positions thereon for supporting nuclear fuel pellets of different diameters between and on adjacent longitudinal portions of the plates located in the inspection chamber of the apparatus.

More particularly, the plates have aperture means in the form of slots and edge cutouts defined therethrough. The slots and cutouts underlie a pellet supported at the adjacent longitudinal portions of the plates and expose portions of the support substrate wall sections which also underlie the pellet such that acoustical energy can be propagated to and from bottom and side portions of the pellet adjacent the longitudinal portions of the plates via reflection of the acoustical energy from the exposed support substrate wall section portions.

The present invention also relates to an apparatus for inspecting nuclear fuel pellets for surface defects which has the combination of: (a) an inspection chamber; (b) a pellet guide chute assembly as defined above extending through the inspection chamber; (c) an acoustical energy reflecting cover disposed over the guide chute assembly at the inspection chamber; and (d) means for transmitting and receiving acoustical energy into and from the inspection chamber for propagating such energy to and from the pellet therein. The apparatus also includes an arrangement associated with the inspection chamber for sensing the position of the pellet as the same slides under the influence of gravity on the guide chute assembly along a longitudinal path through the inspection chamber.

More particularly, the support substrate has an elongated opening defined therethrough being aligned with the aperture means of the plates and extending along the longitudinal path of the pellet through the inspection chamber. The cover has a plurality of openings defined therethrough in spaced apart relation along the longitudinal path of the pellet through the inspection chamber.

Further, the pellet position sensing arrangement includes light transmitting means disposed at the exterior of the substrate and aligned with the elongated opening therethrough for transmitting light through the opening and across the inspection chamber, and light receiving means disposed at the exterior of the cover and aligned with the openings therethrough for receiving light transmitted through the cover openings from across the inspection chamber by the light transmitting means.

These and other advantages and attainments of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which:

FIG. 5 is another perspective view similar to that of FIG. 4, except showing the guide chute assembly in assembled form.

FIGS. 6 and 7 are end views of the chute of FIG. 5, showing a pair of adjustable plates of the guide chute assembly at different locations on a support substrate thereof for positioning pellets of different diameters for inspection.

DETAILED DESCRIPTION OF THE INVENTION

Figure 2:
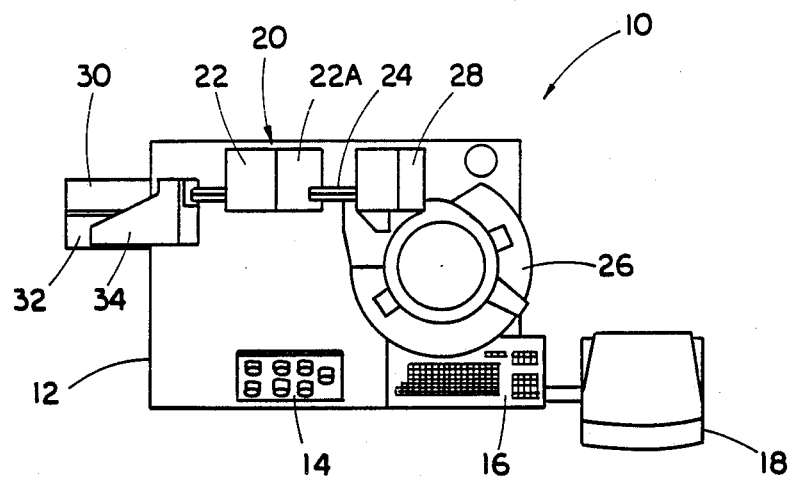
FIG. 2 is a top plan view of the prior art inspection apparatus of FIG. 1.
Figure 1:
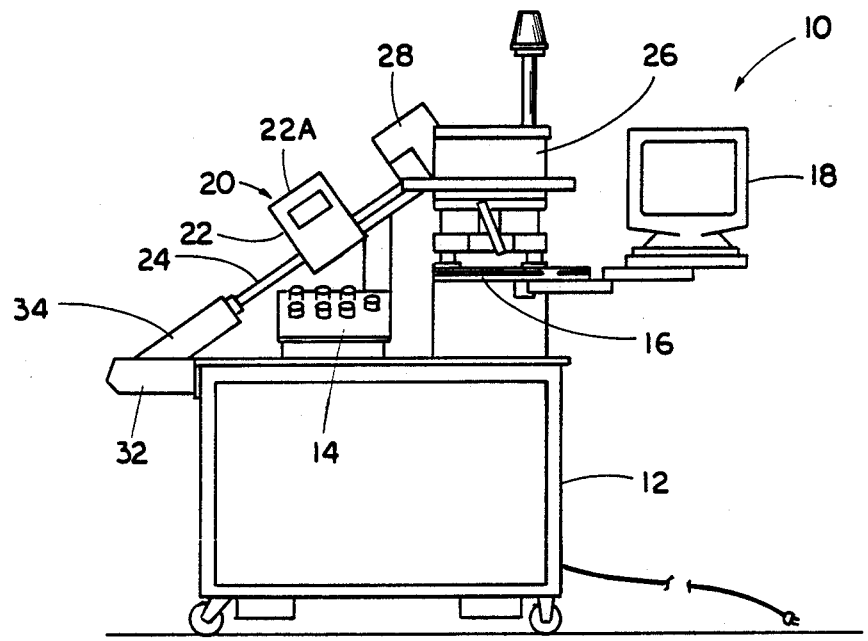
FIG. 1 is an elevational view of a parts shape inspection apparatus of the prior art.

In the following description, like reference characters designate like or corresponding parts throughout the several views of the drawings. Also in the following description, it is to be understood that such terms as "forward", "rearward", "left", "right", "upwardly", "downwardly", and the like, are words of convenience and are not to be construed as limiting terms.

In General

Referring now to the drawings, and particularly to FIGS. and 2, there is shown a prior art inspection apparatus, being generally designated by the numeral 10 and sold by Cochlea Corporation, for inspecting the shapes of small parts and sorting parts with good shapes from those with bad ones. In its basic arrangement the inspection apparatus 10 includes a wheeled base 12 and a console 14, a built-in microprocessor-based computer system (not shown) and video display terminal (VDT) keyboard 16 and VDT monitor 18 mounted on the base 12.

Also, the prior art inspection apparatus 10 includes an inspection chamber 20 having an ultrasonic inspection head 22 (FIGS. 14–16), a heated air system (not shown) for maintaining the inspection chamber 20 and head 22 in the desired operating temperature range. Further, the inspection apparatus 10 includes an inclined inspection track or chute 24 upon which parts are fed from a vibratory bowl feeder 26 by a singulation device 28. The parts slide in single file fashion down the chute 24 under the influence of gravity past the inspection head 22. At the lower end of the chute 24 is positioned two bins, one bin 30 for good parts and one bin 32 for bad parts, and a flipper device 34 being operable for directing the parts to the correct one of the bins 30,32 as determined by the results of the inspection.

In operation, the prior art inspection apparatus 10 carries out acoustical inspection of the shapes of the parts one at a time as they pass through the inspection chamber 20. Basically, the computer system of the inspection apparatus 10 is taught the shape and orientation of a part having the desired or optimum configuration or shape during an initial "learn mode." Sound waves reflected from any subsequent part being inspected are received by an array of transducers 36 making up the ultrasonic inspection head 22. One or the transducers 36A transmits sound waves, whereas the rest of the transducers 36B receive the reflected sound waves.

Based on these reflected sound waves, the receiving transducers 36B of the inspection head 22 generate an "acoustic signature" of the part. The microprocessor based computer system interprets these signatures. Each part thus generates a unique signature and only parts identical to those programmed in the "learn mode" can create the same signature. Defect-free parts are thus determined by comparing the acoustic signatures of parts being inspected to the signatures generated earlier during the "learn mode." Parts whose signatures do not conform to the "learned" signature are rejected as defective and diverted by the flipper 34 into the bad parts bin 32. Good parts are not diverted and go into the good parts bin 30.

The details of how part shape is acoustically detected by the inspection head 22 and analyzed by the computer system of the prior art inspection apparatus 10 need not be described herein in any greater detail since the modifications made to the prior art apparatus 10 in accordance with the principles of the present invention to adapt it for use in inspecting nuclear fuel pellets do not relate to such details. In fact, the modified apparatus operates in this regard the same as the prior art inspection apparatus 10 sold by Cochlea Corporation. Therefore, further description of these details would not contribute to gaining a thorough understanding of the improvements of the present invention which will be described below. Reference can be made to the above-cited U.S. patents assigned to Cochlea Corporation and to the Inspector General User's Guide for gaining a detailed description of such details.

Improved Components of the Present Invention

In place of the vibratory bowl feeder 26, the inspection chute 24, the flipper device 34, and the good and bad parts bins 30,32, the prior art inspection apparatus 10 is modified in accordance with the principles of the present invention to adapt it to inspect nuclear fuel pellets 38 by substituting a single pellet feeder, a pellet guide chute assembly 40 and a pellet discharge conveyor. The single pellet feeder and pellet discharge conveyor which do not form part of the present invention need not be illustrated and described herein to gain a complete and thorough understanding of the improvements provided by the present invention. In operation, a modified inspection apparatus using most of the earlier-described prior art components in conjunction with these improved substituted ones can carry out acoustical inspection of nuclear fuel pellets 12 one at a time for circumferential or surface defects, such as chips and cracks.

Figure 3:
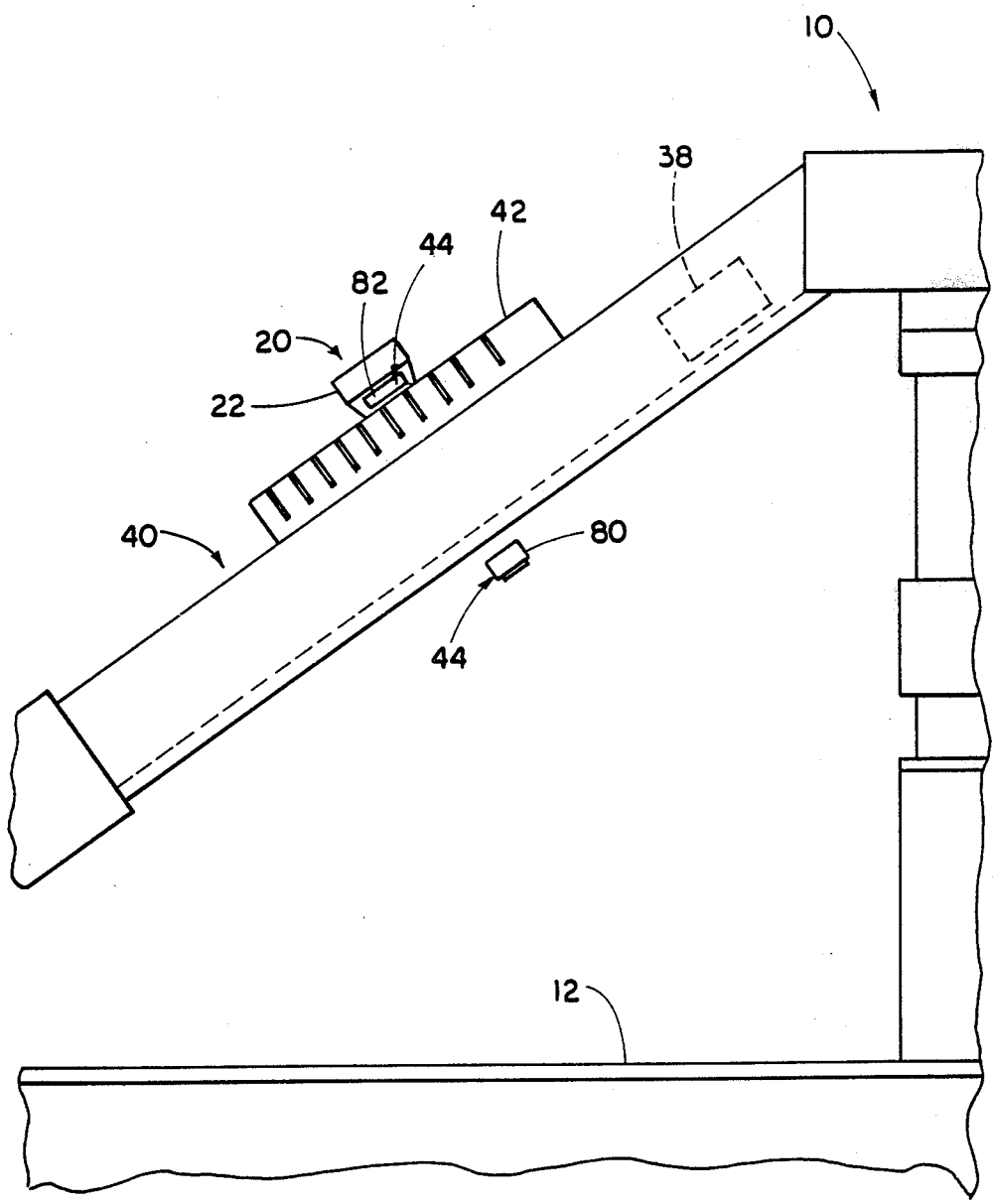
FIG. 3 is an enlarged side elevational view of a pellet guide chute assembly, a pellet position sensing arrangement and an ultrasonic inspection head for modifying the prior art inspection apparatus of FIG. 1 for inspection of nuclear fuel pellets.
Figure 4:
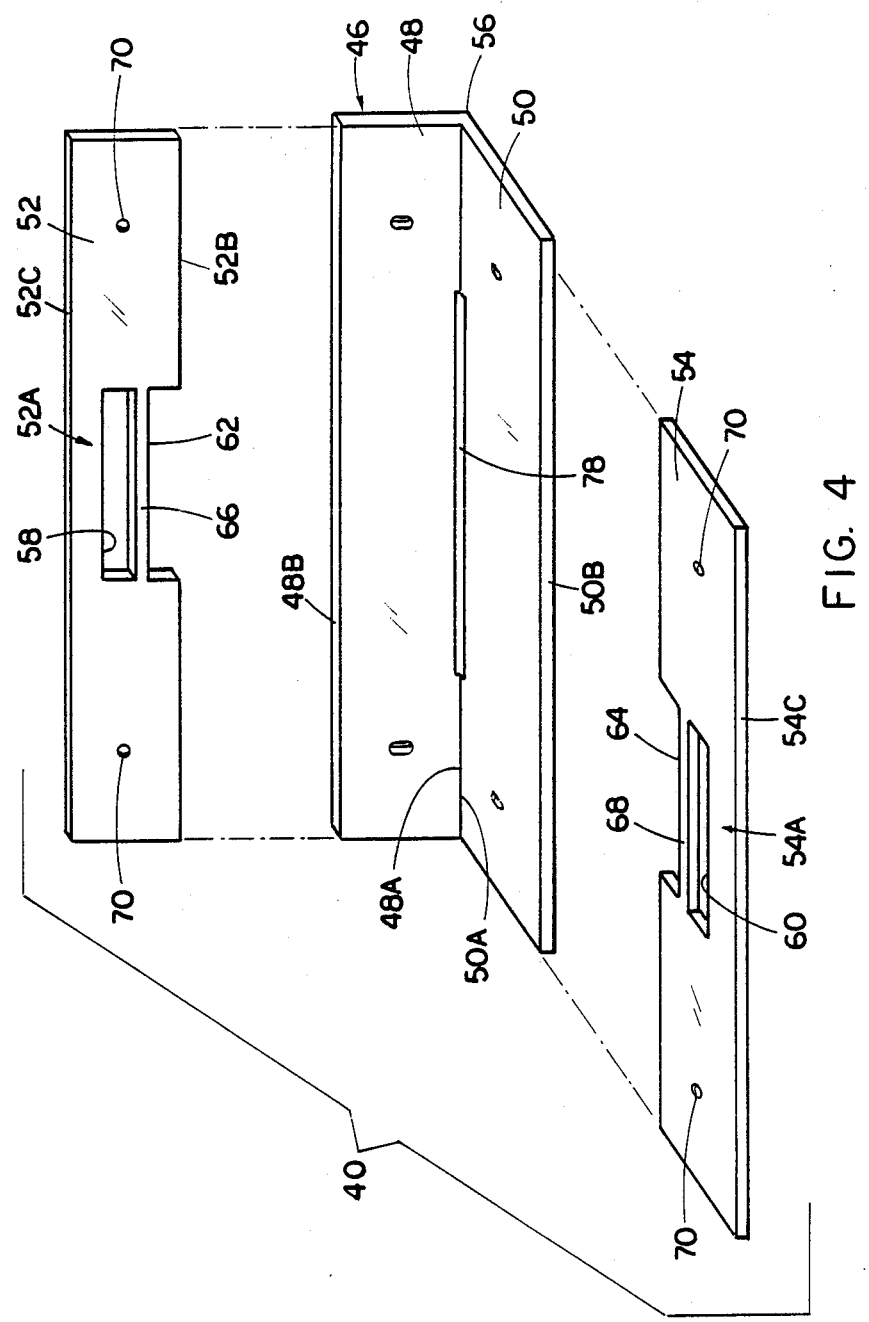
FIG. 4 is a perspective view of the pellet guide chute assembly of FIG. 3, being shown in exploded, unassembled form.
Figure 10:
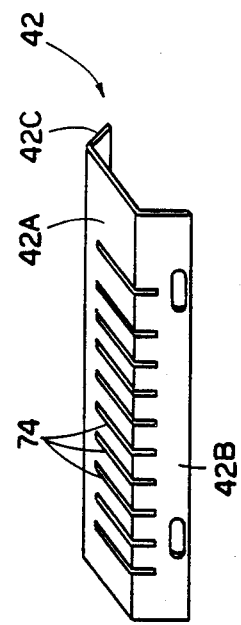
FIG. 10 is a perspective view of a cover for use on the guide chute assembly of FIG. 8 over the inspection chamber.
Figure 11:
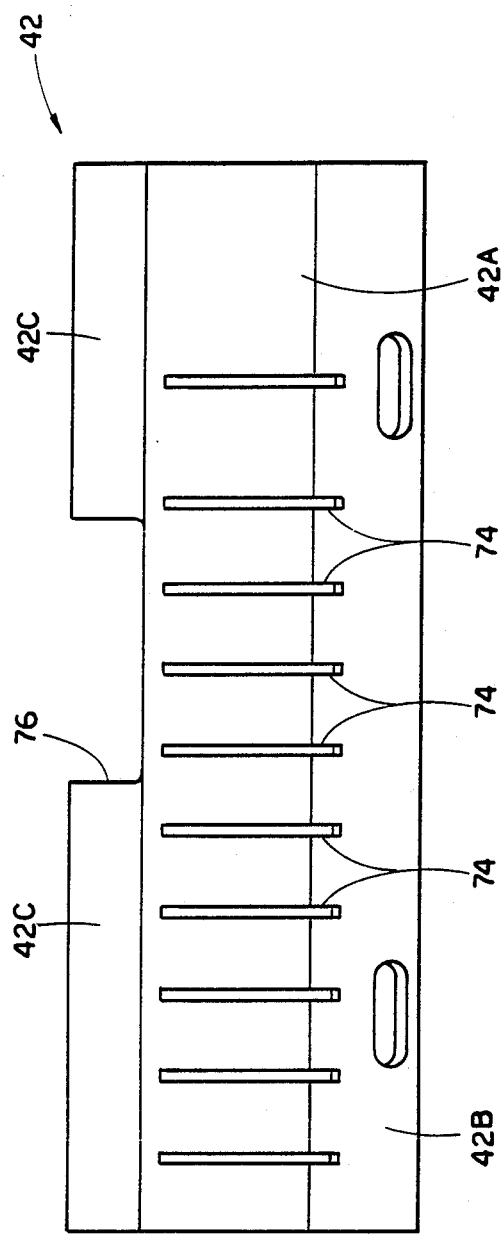
FIG. 11 is an enlarged top plan view of the guide chute assembly cover of FIG. 10.
Figure 12:
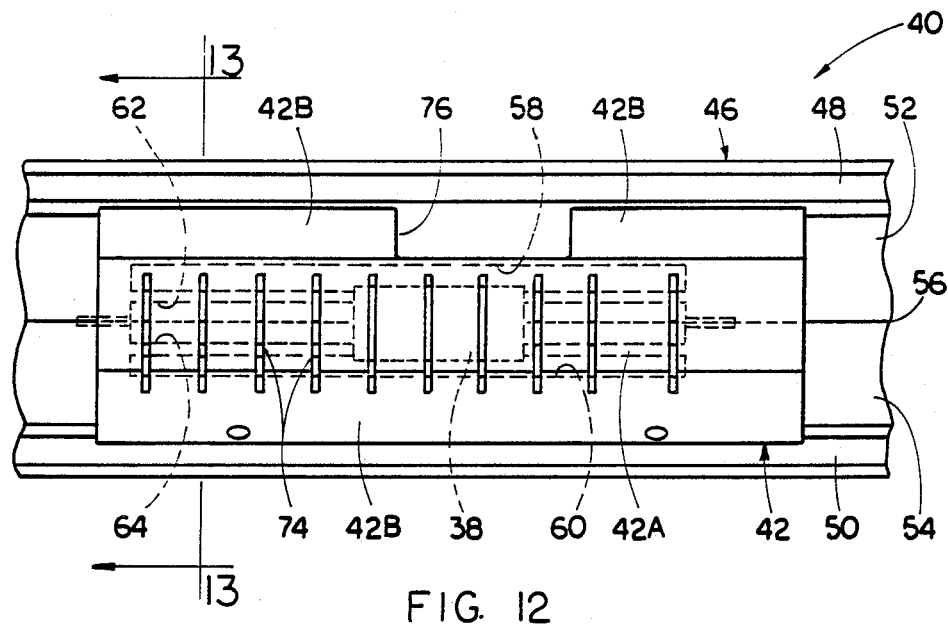
FIG. 12 is another top plan view similar to that of FIG. 8, with the cover of FIG. 10 mounted thereon.
Figure 13:
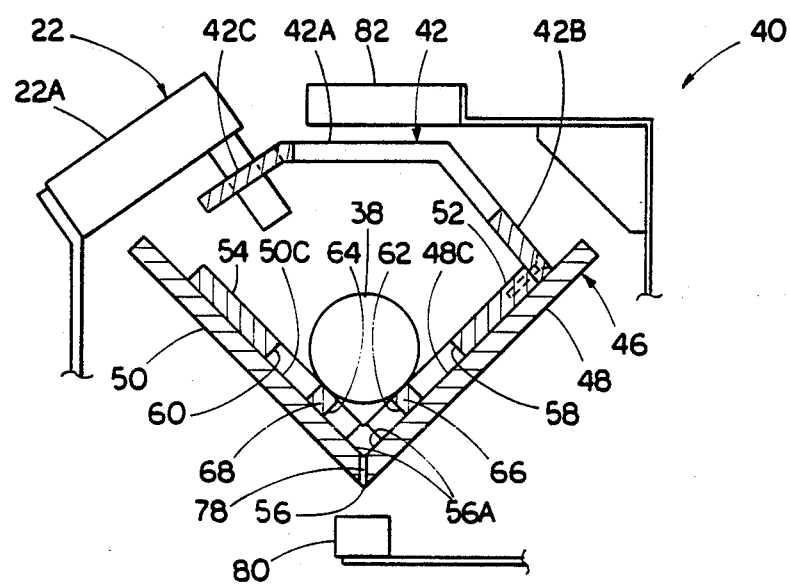
FIG. 13 is a cross-sectional view of the covered chute taken along line 13—13 of FIG. 12.

As seen generally in FIG. 3, the improvements incorporated by the modified inspection apparatus basically relate to the pellet guide chute assembly 40 (see also FIGS. 4–9) disposed in an inclined fashion (similar to the prior art inspection chute 24), and to a cover 42 (see also FIGS. 10 to 12) overlying the chute assembly 40 at the inspection chamber 20 adjacent the inspection head 22 and a pellet position sensing arrangement 44 (see also FIG. 13) being positioned at the inspection chamber 20 and the inspection head 22 along the chute assembly 40.

Referring now to FIGS. 4 to 9, there is shown the pellet guide chute assembly 40 in greater detail. The guide chute assembly 40 as before is inclined and extends through the inspection chamber 20. In its basic components, the guide chute assembly 40 includes a support substrate 46 composed of a pair of elongated wall sections 48,50, and a pair of elongated plates 52,54.

More particularly, the wall sections 48,50 of the chute assembly substrate 40 each have a pair of opposite spaced longitudinal edges 48A,48B and 50A,50B. The wall sections 48,50 are rigidly attached together along inner or adjacent ones 48A,50A of their longitudinal edges to form a corner 56 and are angularly displaced from one another at outer or remote ones 48B,50B of the longitudinal edges to provide the substrate 40 with a generally ninety-degree, V-shaped configuration in cross section. The plates 52,54 are attached on respective upper adjacent sides of the support substrate wall sections 48,50 for supporting a nuclear fuel pellet 38 between and on adjacent longitudinal portions 52A,54A of the plates being located within the inspection chamber 20.

Still further, the plates 52,54 have aperture means in the form of slots 58,60 and cutout regions 62,64 underlying the pellet 38 at the respective adjacent longitudinal portions 52A,54A of the plates. The slots 58,60 and cutout regions 62,64 which are defined through the plates 52,54 expose respective upper side portions 48C,50C and an interior corner portion 56A of the support substrate wall sections 48,50 also underlying the pellet to the interior of the inspection chamber 20 such that acoustical energy can be propagated to and from bottom and side portions 38A,38B of the pellet 38 resting adjacent the respective longitudinal portions 52A,54A of the plates via reflection of the acoustical energy from the exposed support substrate wall section side and corner portions 48C,50C and 56A.

Figure 8:
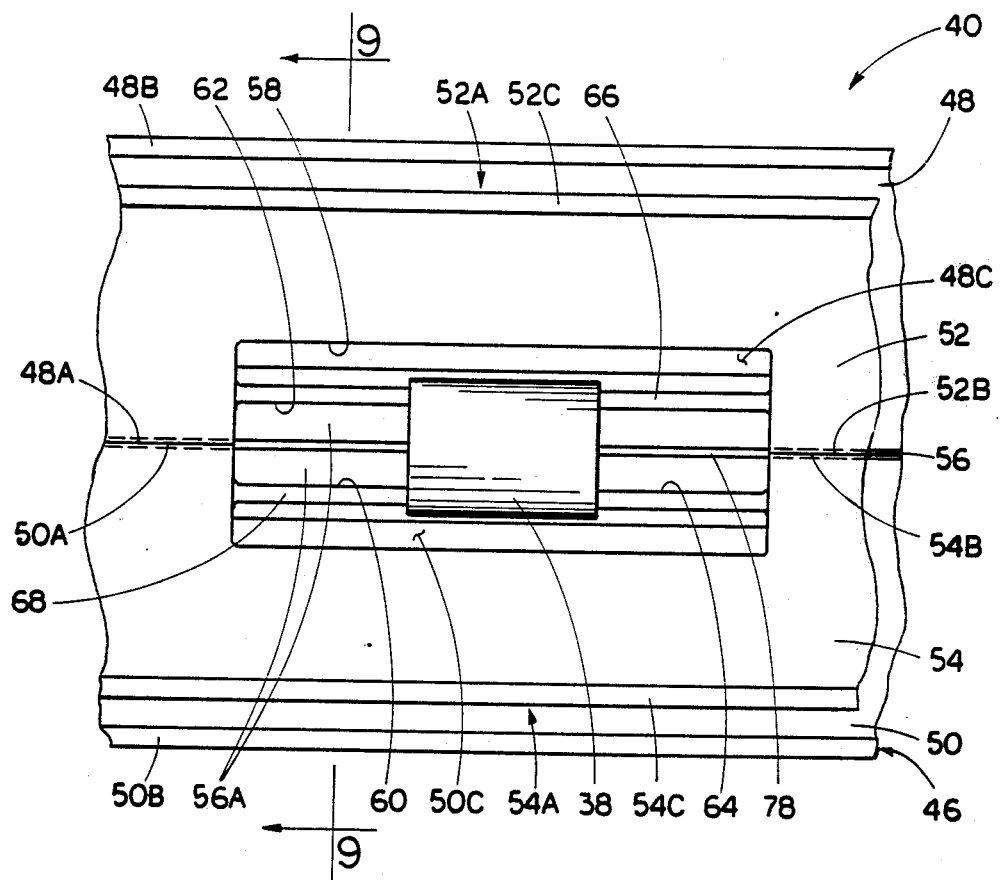
FIG. 8 is a fragmentary top plan view of the chute of FIG. 5, showing a pellet in an inspection chamber.
Figure 9:
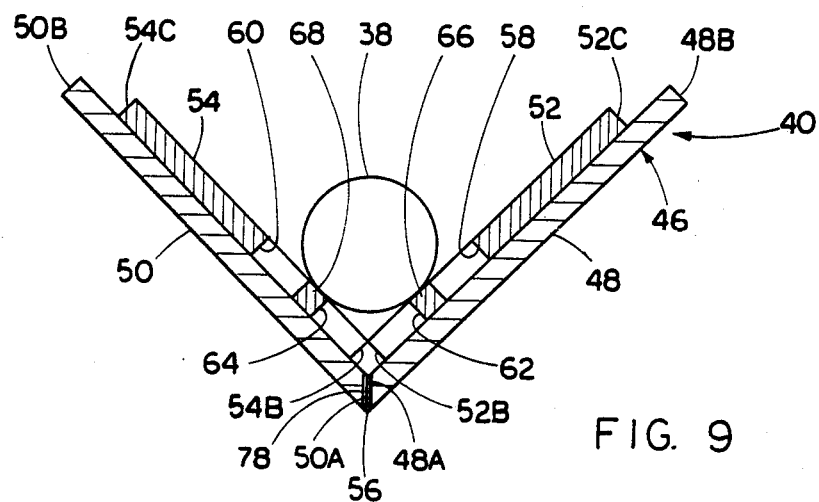
FIG. 9 is a cross-sectional view of the guide chute assembly taken along line 9—9 of FIG. 8.

The respective cutout regions 62,64 are defined in inner or adjacent ones 52B,54B of opposite longitudinal edges of the plates 52,54 at adjacent longitudinal portions 52A,54A thereof, whereas the respective slots 58,60 are defined between and spaced from the cutout regions 62,64 and the outer or remote ones 52C,54C of the longitudinal edges of the plates. The spaced slots 58,60 and cutout regions 62,64 of the respective plates 52,54 define ligaments 66,68 in the plates 52,54 therebetween at the adjacent longitudinal plate portions 52A,54A upon which the pellet 38 rests, as can be seen in FIGS. 8 and 9.

FIGS. 6 to 9 also illustrate means for adjustably attaching the plates 52,54 to the upper adjacent sides of the support substrate wall sections 48,50 for allowing sliding lateral movement thereon toward and away from the adjacent longitudinal edges 48A,50A of the wall sections 48,50. Such adjustability of the plates 52,54 allows relocation of the plates to the desired stationary positions thereon for supporting nuclear fuel pellets of different diameters between and on the ligaments 66,68 of the adjacent longitudinal portions 52A,54A of the plates being located in the inspection chamber 20 of the modified inspection apparatus. Specifically, lateral movement of the plates 52,54 correspondingly lengthens or shortens the distance between their ligaments 66,68 to accommodate placement thereon of pellets 38 having different diameters.

More particularly, the attaching means of the glide chute assembly 40 for adjustably attaching the plates 52,54 to the wall sections 48,50 of the support substrate 46 include a plurality of elongated holes 70 in the form of elongated slots defined through the plates 52,54 and a plurality of removable fasteners 72 inserted through the holes 70 and threadably anchored to the wall sections 48,50. The fasteners 72 can be turned to partially unthread them from the wall sections 48,50 and loosen the plates 52,54 for adjustment. Then, once the plates 52,54 have been slidably moved to the desired positions, the fasteners 72 are retightened to reattach the plates at the desired stationary positions on the support substrate wall sections 48,50.

Figure 15:
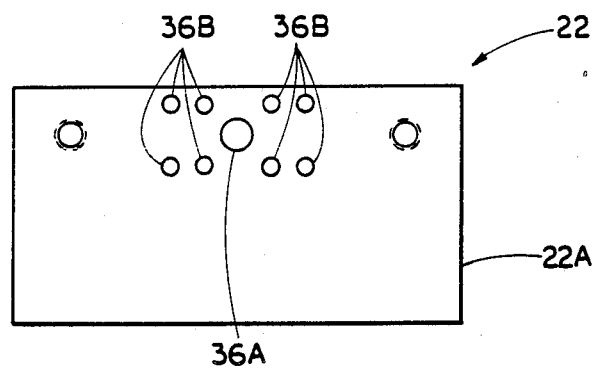
FIG. 15 is a top plan view of the ultrasonic inspection head as seen along line 15—15 of FIG. 14.
Figure 14:
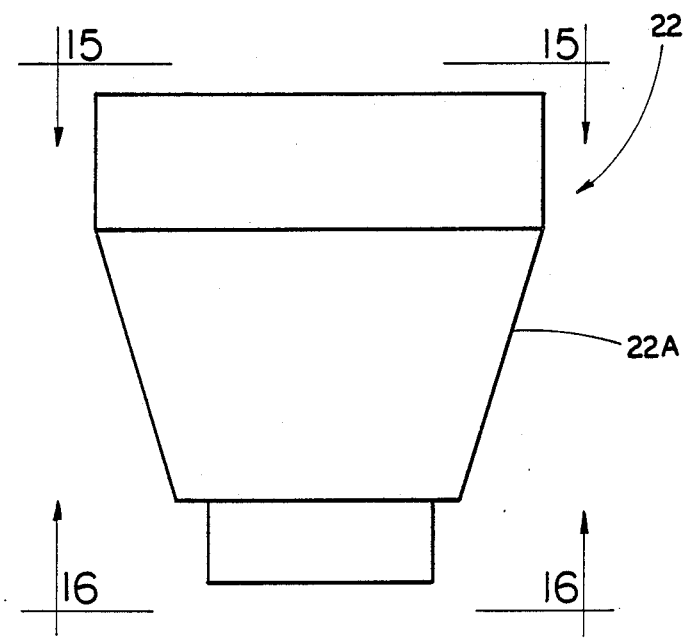
FIG. 14 is a side elevational view of the ultrasonic inspection head of FIG. 3.
Figure 16:
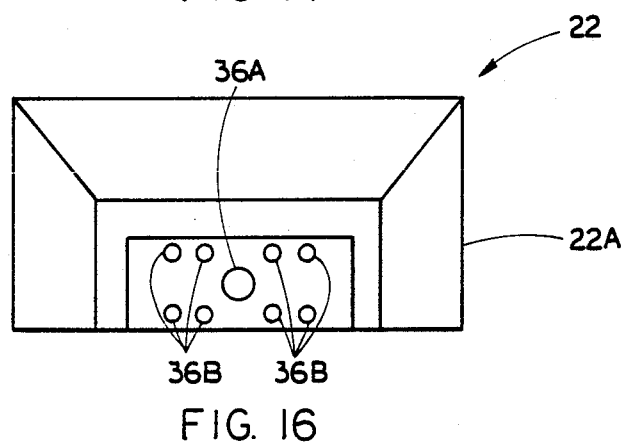
FIG. 16 is a bottom plan view of the ultrasonic inspection head as seen along line 16—16 of FIG. 14.

Also, in the modified inspection apparatus, the cover 42 has a planar central section 42A and opposite downturned opposite edges 42B,42C applied over the guide chute assembly 40 at the inspection chamber 20. The cover 42 provides a means for reflecting and confining the acoustical energy within the inspection chamber. The cover 42 contains a plurality of openings in the form of elongated slots 74 defined through the cover 42 so as to extend generally parallel to one another and generally perpendicular to a longitudinal path of sliding movement of the pellet 38 down the inclined chute assembly 40 through the inspection chamber 20. The cover 42 also has an opening or notch 76 defined therethrough which receives the ultrasonic inspection head 22 having a housing 22A mounting the acoustical energy transmitting and receiving transducers 36A,36B, as best seen in FIGS. 14 to 16, for transmitting acoustical energy into and receive it from the inspection chamber 20 for propagating such energy to and from the pellet 38 therein.

The pellet position sensing arrangement 44 of the modified inspection apparatus is associated with the support substrate 46 and the cover 42 at the inspection chamber 20 for sensing the position of the pellet 38 as the same slides under the influence of gravity down the inclined guide chute assembly 40 along the longitudinal path through the inspection chamber. Specifically, the support substrate 46 has an elongated opening or slit 78 defined therethrough at its corner 56 and being aligned with the cutout regions 62,64 of the plates 52,54 so as to extend along the longitudinal path of the pellet 38 through the inspection chamber 20. As mentioned above, the slots 74 in the cover 42 are spaced apart along longitudinal path of the pellet through the inspection chamber 20.

The pellet position sensing arrangement 44 includes a light transmitting device 80 disposed at the exterior of the substrate corner 56 and aligned with elongated slit 78 therethrough for transmitting light through the open slit and across the inspection chamber 20. The arrangement 44 also includes a plurality of light receiving devices 82 disposed at the exterior of the cover 42 and aligned with the respective slots 74 therethrough for receiving light transmitted through the cover slots 74 from across the inspection chamber 20 by the light transmitting device 80.

As mentioned above, the elongated substrate slit 78 is defined through the corner 56 of the substrate 46 formed by the rigidly attached wall sections 48,50 thereof. The interior corner portion 56A exposed by the adjacent cutout regions 62,64 of the plates 52,54 not only underlies the adjacent cutout regions but also contains the elongated open slit 78 in the substrate 46. The elongated slit also underlies the bottom of the pellet 38 being supported between the adjacent longitudinal portions 52A,54A of the plates 52,54 such that path of the light transmitted by the light transmitting device 80 to the light receiving devices 82 is interrupted by the pellet 38 as the latter slides along its longitudinal path between the devices 80,82.

It is thought that the present invention and many of its attendant advantages will be understood from the foregoing description and it will be apparent that various changes may be made in the form, construction and arrangement thereof without departing from the spirit and scope of the invention or sacrificing all of its material advantages, the form hereinbefore described being merely a preferred or exemplary embodiment thereof.

I claim:

1. In an apparatus for inspecting nuclear fuel pellets for surface defects, the combination comprising:
   (a) an inspection chamber;
   (b) a pellet guide chute assembly extending through said inspection chamber and including
      (i) a support substrate composed of a pair of elongated wall sections rigidly attached together to have a generally V-shaped configuration in cross section, and
      (ii) a pair of elongated plates attached on respective upper adjacent sides of said support substrate wall sections for supporting a nuclear fuel pellet between and on adjacent longitudinal portions of said plates located in said inspection chamber,
      (iii) said plates having aperture means underlying the pellet at said adjacent longitudinal portions of said plates which expose portions of said support substrate wall sections also underlying the pellet such that acoustical energy can be propagated to and from bottom and side portions of the pellet adjacent said adjacent longitudinal portions of said plates via reflection of the acoustical energy from said exposed support substrate wall section portions;
   (c) an acoustical energy reflecting cover disposed over said guide chute assembly at said inspection chamber; and
   (d) means for transmitting and receiving acoustical energy into and from said inspection chamber for propagating such energy to and from the pellet therein.

2. The apparatus as recited in claim 1, wherein:
said plates have respective pairs of opposite spaced longitudinal edges; and
said aperture means are respective elongated slots defined through said plates at said adjacent longitudinal portions of said plates between and spaced from said longitudinal edges thereof, said slots of said plates exposing side portions of said support substrate wall sections which underlie said slots of said plates and underlie sides of the pellet being supported between said adjacent longitudinal portions of said plates such that acoustical energy can be propagated to and from the pellet sides via reflection from said exposed side portions of said support substrate wall sections.

3. The apparatus as recited in claim 1, wherein:
said plates have respective pairs of opposite spaced longitudinal edges; and
said aperture means are respective cutout regions defined in adjacent ones of said longitudinal edges of said plates at said adjacent longitudinal portions thereof, said adjacent cutout regions of said plates exposing an interior corner portion of said support substrate wall sections which underlies said adjacent cutout regions of said plates and underlies a bottom of the pellet being supported between said adjacent longitudinal portions of said plates such that acoustical energy can be propagated to and from the pellet bottom via reflection from said exposed corner portion of said support substrate wall sections.

4. The apparatus as recited in claim 3, wherein said aperture means further are respective elongated slots defined through said plates at said adjacent longitudinal portions of said plates between and spaced from said cutout regions and said remote longitudinal edges thereof, said slots of said plates exposing side portions of said support substrate wall sections which underlie said slots of said plates and underlie sides of the pellet being supported between said adjacent longitudinal portions of said plates such that acoustical energy can be propagated to and from the pellet sides via reflection from said exposed side portions of said support substrate wall sections.

5. The apparatus as recited in claim 1, wherein said chute assembly also includes means for adjustably attaching said plates to said wall sections of said support substrate for sliding lateral movement thereon to locate said plates at desired stationary positions for supporting nuclear fuel pellets of different diameters between said adjacent longitudinal portions of said plates located in said inspection chamber.

6. The apparatus as recited in claim 5, wherein means for adjustably attaching said plates to said wall sections of said support substrate include a plurality of elongated holes defined in one of said support substrate wall sections and said plates and a plurality of removable fasteners adapted to be inserted through said holes and anchored to the other of said support substrate wall sections and said plates for stationarily mounting said plates at said desired stationary positions on said support substrate wall sections.

7. The apparatus as recited in claim 1, further comprising an arrangement associated with said inspection chamber for sensing the position of the pellet as the same slides under the influence of gravity on said guide chute assembly along a longitudinal path through said inspection chamber.

8. The apparatus as recited in claim 7, wherein:
said support substrate has an elongated opening defined therethrough being aligned with said aperture means of said plates and extending along said longitudinal path of the pellet through said inspection chamber;
said cover has a plurality of openings defined therethrough in spaced apart relation along said longitudinal path of the pellet through said inspection chamber; and
said arrangement includes light transmitting means disposed at the exterior of said substrate and aligned said elongated opening therethrough for transmitting light through said opening and across said inspection chamber, and light receiving means disposed at the exterior of said cover and aligned with said openings therethrough for receiving light transmitted through said cover openings from across said inspection chamber by said light transmitting means.

9. The apparatus as recited in claim 8, wherein said light receiving means includes a plurality of light receivers, each being aligned with one of said cover openings.

10. The apparatus as recited in claim 8, wherein said substrate elongated opening is defined through a corner of said substrate formed by said rigidly attached wall sections thereof.

11. The apparatus as recited in claim 10, wherein:
said plates have respective pairs of opposite spaced longitudinal edges; and
said aperture means are respective cutout regions defined in adjacent ones of said longitudinal edges of said plates at said adjacent longitudinal portions thereof, said adjacent cutout regions of said plates exposing an interior portion of said corner of said support substrate wall sections which underlies said adjacent cutout regions of said plates and contains said elongated opening in said substrate and which underlies a bottom of the pellet being supported between said adjacent longitudinal portions of said plates such that acoustical energy can be propagated to and from the pellet bottom via reflection from said exposed corner portion of said support substrate wall sections.

12. The apparatus as recited in claim 8, wherein said plurality of cover openings are in the form of a plurality of elongated slots formed in said cover so as to extend generally parallel to one another and generally perpendicular to said longitudinal path of the pellet through said inspection chamber.

13. The apparatus as recited in claim 1, wherein said cover has an opening defined therethrough receiving said acoustical energy transmitting and receiving means.

* * * * *